(12) United States Patent
Hinayama et al.

(10) Patent No.: US 9,925,294 B2
(45) Date of Patent: Mar. 27, 2018

(54) WATER-ABSORBENT RESIN AND ABSORBENT ARTICLE

(71) Applicant: Sumitomo Seika Chemicals Co. Ltd., Kako-gun (JP)

(72) Inventors: Tetsuhiro Hinayama, Himeji (JP); Masahiro Murakami, Himeji (JP); Hiroki Yabuguchi, Himeji (JP); Hideki Yokoyama, Himeji (JP)

(73) Assignee: Sumitomo Seika Chemicals Co. Ltd., Kako-gun (JP)

( * ) Notice: Subject to any disclaimer, the term of this patent is extended or adjusted under 35 U.S.C. 154(b) by 0 days.

(21) Appl. No.: 14/903,879

(22) PCT Filed: Nov. 4, 2014

(86) PCT No.: PCT/JP2014/079247
§ 371 (c)(1),
(2) Date: Jan. 8, 2016

(87) PCT Pub. No.: WO2016/006134
PCT Pub. Date: Jan. 14, 2016

(65) Prior Publication Data
US 2016/0367717 A1    Dec. 22, 2016

(30) Foreign Application Priority Data

Jul. 11, 2014  (JP) .................................. 2014-143719
Oct. 31, 2014  (JP) .................................. 2014-223726

(51) Int. Cl.
*A61L 15/24*  (2006.01)
*A61L 15/20*  (2006.01)
(Continued)

(52) U.S. Cl.
CPC .............. *A61L 15/24* (2013.01); *A61F 13/49* (2013.01); *A61F 13/53* (2013.01); *A61L 15/20* (2013.01);
(Continued)

(58) Field of Classification Search
CPC .................................................... C08F 299/00
See application file for complete search history.

(56) References Cited

U.S. PATENT DOCUMENTS

| 5,422,405 A | 6/1995 | Dairoku et al. |
| 6,444,744 B1 | 9/2002 | Fujimaru et al. |

(Continued)

FOREIGN PATENT DOCUMENTS

| CN | 1615318 A | 5/2005 |
| EP | 0068189 A1 | 1/1983 |

(Continued)

OTHER PUBLICATIONS

English translation (human translation) of JP 2012-236898 A to Handa et al. (Year: 2012).*

(Continued)

*Primary Examiner* — Randy P Gulakowski
*Assistant Examiner* — Ha S Nguyen
(74) *Attorney, Agent, or Firm* — Locke Lord LLP

(57) ABSTRACT

Provided are a water-absorbent resin having better water-absorption performance and being prevented from discoloring before and after storage for a long time under high temperature and high humidity, and an absorbent article including the absorbent resin. The water-absorbent resin according to the present invention is prepared by polymerizing a water-soluble ethylenically unsaturated monomer in the presence of an internal-crosslinking agent and performing post-crosslinking with a post-crosslinking agent, wherein the water-absorbent resin satisfies the following (Continued)

properties: (A) a water-absorption capacity of physiological saline of 55 g/g or more, a water-absorption capacity of physiological saline under a load of 4.14 kPa of 15 mL/g or more, and a residual monomer content of 300 ppm or less; and (B) a yellow index of 5.0 or less and a yellow index change ratio (ΔYI) after leaving for 10 days under 70° C. and 90% RH of 10 or less.

4 Claims, 1 Drawing Sheet

(51) Int. Cl.
    *A61F 13/53*     (2006.01)
    *A61F 13/49*     (2006.01)
    *C08F 299/00*     (2006.01)
    *C08F 8/00*     (2006.01)
    *C08F 2/32*     (2006.01)
    *C08F 20/06*     (2006.01)

(52) U.S. Cl.
    CPC .................. *C08F 2/32* (2013.01); *C08F 8/00* (2013.01); *C08F 20/06* (2013.01); *C08F 299/00* (2013.01)

(56) References Cited

U.S. PATENT DOCUMENTS

| | | |
|---|---|---|
| 6,469,080 B2 | 10/2002 | Miyake et al. |
| 6,964,998 B2 | 11/2005 | Wada et al. |
| 7,193,006 B2 | 3/2007 | Ishizaki et al. |
| 9,006,134 B2 | 4/2015 | Nagasawa et al. |
| 2001/0053807 A1 | 12/2001 | Miyake et al. |
| 2004/0110006 A1 | 6/2004 | Ishizaki et al. |
| 2005/0085604 A1* | 4/2005 | Handa ..................... A61L 15/18 526/227 |
| 2009/0275470 A1 | 11/2009 | Nagasawa et al. |
| 2013/0158495 A1 | 6/2013 | Handa et al. |
| 2015/0216740 A1 | 8/2015 | Watanabe et al. |

FOREIGN PATENT DOCUMENTS

| | | |
|---|---|---|
| EP | 0288865 A2 | 11/1988 |
| EP | 0942014 A2 | 9/1999 |
| EP | 1108745 A1 | 6/2001 |
| EP | 2615117 A1 | 7/2013 |
| JP | S61-271303 A | 12/1986 |
| JP | 64-038406 A | 2/1989 |
| JP | 05-086251 A | 4/1993 |
| JP | 06-184320 A | 7/1994 |
| JP | 11-322846 A | 11/1999 |
| JP | H11-335404 A | 12/1999 |
| JP | 2000-026510 A | 1/2000 |
| JP | 2000-230129 A | 8/2000 |
| JP | 2000-327926 A | 11/2000 |
| JP | 2001-234087 A | 8/2001 |
| JP | 2003-206381 A | 7/2003 |
| JP | 2003-246810 A | 9/2003 |
| JP | 2004-197087 A | 7/2004 |
| JP | 2006-176570 A | 7/2006 |
| JP | 2006-521431 A | 9/2006 |
| JP | 2006-522181 | 9/2006 |
| JP | 2008-133396 A | 6/2008 |
| JP | 2008-535640 A | 9/2008 |
| JP | 2009-280668 A | 12/2009 |
| JP | 2012-031292 A | 2/2012 |
| JP | 2012-236898 A | 12/2012 |
| JP | 2012236898 A * | 12/2012 |
| WO | WO-03/051940 A1 | 6/2003 |
| WO | 03/059961 A1 | 7/2003 |
| WO | WO-2004/084962 A1 | 10/2004 |
| WO | WO-2004/085496 A1 | 10/2004 |
| WO | WO-2006/109882 A1 | 10/2006 |
| WO | WO-2009/005114 A1 | 1/2009 |
| WO | WO-2012/033025 A1 | 3/2012 |
| WO | WO-2014/038324 A1 | 3/2014 |

OTHER PUBLICATIONS

European Search Report dated Jun. 22, 2016, issued for European patent application No. 14893695.8.
Office Action dated Jul. 12, 2016, issued for European patent application No. 14893695.8.
Modern Superabsorbent Polymer Technology, Edited by Fredric L. Buchholz et al., Wiley-VCH, pp. 101, 152,178 and 213.
Opposition dated Apr. 11, 2016, issued for Japanese Patent No. 5766344.
Office Action dated Aug. 17, 2016, issued for Chinese Patent Application No. 201480017968.3 and English translation thereof.
Observations by a third party for European Patent Application No. 14893695.8 dated Jan. 27, 2017.

* cited by examiner

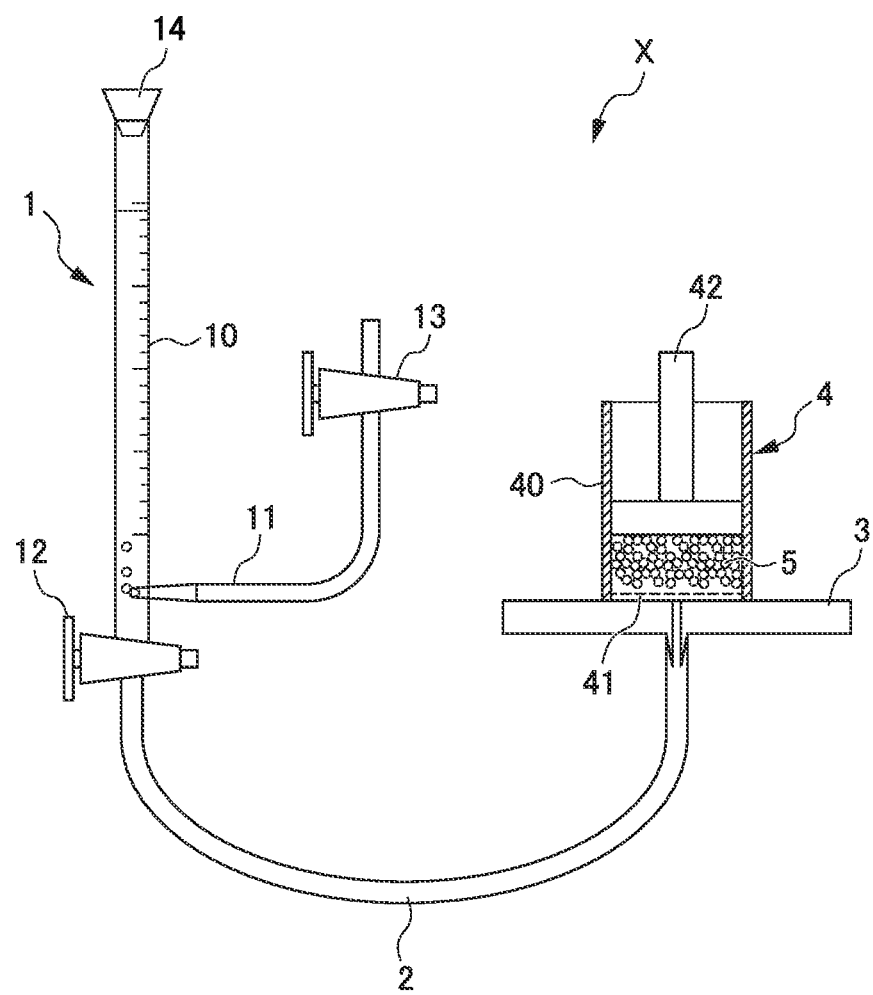

WATER-ABSORBENT RESIN AND ABSORBENT ARTICLE

TECHNICAL FIELD

The present invention relates to a water-absorbent resin and an absorbent article, and more specifically relates to a water-absorbent resin forming an absorbent material suitably used for hygienic materials such as disposable diapers, sanitary napkins, and incontinence pads and an absorbent article including the water-absorbent resin.

BACKGROUND ART

Water-absorbent resins have been widely used in the field of hygienic materials, such as disposable diapers, sanitary napkins, and incontinence pads, by utilizing the characteristics of the water-absorbent resins that large amounts of aqueous liquids, for example, body fluids such as human urine, blood, and sweat, are rapidly absorbed and that the liquids once absorbed are not released even under loads.

For example, crosslinked products of partially neutralized polymers of acrylic acid are preferred as water-absorbent resins because they have many advantages, including the followings: they have better water-absorption performance; their raw materials such as acrylic acid has easy industrial availability, and therefore they can be produced with stable quality and low cost; they show no shortcomings such as in which decomposition is likely to occur; and they are safer products.

These water-absorbent resins are required to have better water-absorption performance. Specifically, it is required to have appropriate liquid-absorbent capacity, water-absorption rate, liquid suction force, water-absorption capacity under a load, gel strength, and so on. In addition to such water-absorption performance, from the viewpoint of being used in absorbent articles requiring cleanliness, such as diapers and sanitary articles, it is required to be less discolored and to be scarcely discolored with passage of time. That is, the water-absorbent resins have problems that they are easily yellowed or browned by external factors, such as heat and humidity, during storage. In particular, in the field of hygienic materials, if a water-absorbent resin in an absorbent article, such as a disposable diaper or a sanitary napkin, is discolored, the commercial value of the article significantly decreases. The water-absorbent resin is therefore required to be scarcely discolored even after storage under a severe environment.

Examples of the technique for preparing a water-absorbent resin having better water-absorption performance include a method of producing a water-absorbent resin by mixing a water-absorbent resin containing carboxyl groups and a plurality of crosslinking agents having different solubility parameters and heating the mixture (see Patent Document 1), a method of producing water-absorbent resin particles by polymerization using a water-soluble azo radical polymerization initiator in the presence of a multivalent glycidyl compound as an internal-crosslinking agent (see Patent Document 2), and a method of producing a water-absorbent resin by performing a polymerization reaction in the presence of a diamine compound or its salt and performing a crosslinking reaction by adding a crosslinking agent after the polymerization (see Patent Document 3). Examples of the water-absorbent resin having a discoloration-preventing effect include a highly water-absorbent polymer composition composed of a highly water-absorbent polymer and an organophosphate compound or its salt (see Patent Document 4), a water-absorbing agent composition including an acid water-swelling crosslinked polymer, a basic water-swelling crosslinked polymer, and a discoloration-preventing agent and/or an antioxidant and/or a boron compound (see Patent Document 5), and a water-absorbing agent composition including a water-absorbent resin, an organic carboxylic acid, and/or its salt (see Patent Document 6).

Patent Document 1: Japanese Unexamined Patent Application, Publication No. H6-184320
Patent Document 2: Japanese Unexamined Patent Application, Publication No. 2006-176570
Patent Document 3: Japanese Unexamined Patent Application, Publication No. 2008-133396
Patent Document 4: Japanese Unexamined Patent Application, Publication No. H5-86251
Patent Document 5: Japanese Unexamined Patent Application, Publication No. 2000-230129
Patent Document 6: Japanese Unexamined Patent Application, Publication No. 2000-327926

DISCLOSURE OF THE INVENTION

Problems to be Solved by the Invention

The present invention has been proposed in view of the foregoing situations, and has an object to provide a water-absorbent resin having better water-absorption performance and being prevented from discoloring before and after storage for a long time under high temperature and high humidity and an absorbent article including the absorbent resin.

Means for Solving the Problems (1) The present invention provides a water-absorbent resin prepared by polymerizing a water-soluble ethylenically unsaturated monomer in the presence of an internal-crosslinking agent and performing post-crosslinking with a post-crosslinking agent, the water-absorbent resin satisfying all of the following properties:

(A) a water-absorption capacity of physiological saline of 55 g/g or more, a water-absorption capacity of physiological saline under a load of 4.14 kPa of 15 mL/g or more, and a residual monomer content of 300 ppm or less; and (B) a yellow index of 5.0 or less and a yellow index change ratio ($\Delta$YI) after leaving for 10 days under 70° C. and 90% RH of 10 or less.

(2) The present invention also provides the water-absorbent resin according to aspect (1), wherein the water-soluble ethylenically unsaturated monomer is at least one selected from the group consisting of (meth)acrylic acid or its salts, (meth)acrylamide, and N,N-dimethylacrylamide.

(3) The present invention also provides the water-absorbent resin according to aspect (1) or (2), having a median particle diameter of 100 to 600 μm.

(4) The present invention also provides a water-absorbent resin prepared by further blending an aminocarboxylic acid compound in the water-absorbent resin according to any one of aspects (1) to (3).

(5) The present invention also provides the water-absorbent resin according to aspect (4), wherein the aminocarboxylic acid compound is at least one selected from the group consisting of diethylenetriaminepentaacetic acid, triethylenetetraminehexaacetic acid, trans-1,2-diaminocyclohexanetetraacetic acid, ethylenediaminetetraacetic acid, and salts thereof.

(6) The present invention provides an absorbent article comprising the water-absorbent resin according to any one of aspects (1) to (5).

Effects of the Invention

The present invention can provide a water-absorbent resin having better water-absorption performance and being prevented from discoloring before and after storage for a long time under high temperature and high humidity and an absorbent article including the absorbent resin.

BRIEF DESCRIPTION OF THE DRAWINGS

FIG. 1 A pattern diagram showing the schematic arrangement of a apparatus for measuring, in a water-absorbent resin, a water-absorption capacity of physiological saline under a load of 4.14 kPa

PREFERRED MODE FOR CARRYING OUT THE INVENTION

The present invention will be described in detail below.

1. Water-Absorbent Resin

The water-absorbent resin according to the present invention has the following properties.

That is, the water-absorbent resin according to the present invention is prepared by polymerizing a water-soluble ethylenically unsaturated monomer in the presence of an internal-crosslinking agent and performing post-crosslinking with a post-crosslinking agent. The water-absorbent resin satisfies all of the following properties:

(A) a water-absorption capacity of physiological saline of 55 g/g or more, a water-absorption capacity of physiological saline under a load of 4.14 kPa of 15 mL/g or more, and a residual monomer content of 300 ppm or less; and (B) a yellow index of 5.0 or less and a yellow index change ratio ($\Delta$YI) after leaving for 10 days under 70° C. and 90% RH of 10 or less.

(A) Water-Absorption Performance

The water-absorbent resin according to the present invention has a water-absorption capacity of physiological saline of 55 g/g or more. The water-absorption capacity of physiological saline refers to the mass of physiological saline that can be absorbed by a water-absorbent resin per unit mass and indicates the degree of the liquid-absorbent capacity of the water-absorbent resin. The water-absorbent resin according to the present invention has a water-absorption capacity of physiological saline of 55 g/g or more, preferably 58 g/g or more, more preferably 60 g/g or more, and further preferably 62 g/g or more, accordingly the absorbent article to which the water-absorbent resin is applied can have a large absorption volume. Since a too high a water-absorption capacity tends to increase the slimy feeling after water-absorption, the upper limit of the water-absorption capacity of physiological saline is preferably 100 g/g or less, more preferably 90 g/g or less, further preferably 85 g/g or less, and further more preferably 80 g/g or less.

The water-absorbent resin according to the present invention has a water-absorption capacity of physiological saline under a load of 4.14 kPa of 15 mL/g or more, preferably 18 mL/g or more, and more preferably 20 mL/g or more. In general, when a pressure is applied to an absorbent material including a water-absorbent resin (for example, when an infant wearing a diaper to which the absorbent material has been employed sits immediately after urination), the re-wet amount of absorbed liquid tends to be increased. This means that a higher water-absorption capacity of physiological saline under a load of 4.14 kPa reduces the re-wet amount when a pressure is applied to a hygienic material containing the water-absorbent resin. The water-absorption capacity of physiological saline under a load of 4.14 kPa is preferably 50 mL/g or less and more preferably 40 mL/g or less.

The water-absorbent resin according to the present invention has a residual monomer content of 300 ppm or less, preferably 200 ppm or less, more preferably 150 ppm or less, further preferably 100 ppm or less, and further more preferably 80 ppm or less. In a polymerized resin, an unreacted monomer may remain. When a water-absorbent resin is used as a raw material of a hygienic material, the residual has a possibility of adversely affecting the skin of a wearer, such as causing a rash. Accordingly, it is desirable to reduce the residual monomer content in a polymerized resin as much as possible.

(B) Yellow Index and Yellow Index Change Ratio

The water-absorbent resin according to the present invention has a yellow index of 5.0 or less and a yellow index change ratio ($\Delta$YI) after leaving for 10 days under 70° C. and 90% RH of 10 or less.

The yellow index can be measured with a color difference meter of which the tristimulus values, X, Y, and Z, were corrected with a white sheet for calibration. From the X, Y, and Z of the water-absorbent resin of a measuring object, the yellow index (YI value) can be calculated by the following formula:

$$\text{Yellow index} = 100(1.28X - 1.06Z)/Y.$$

The water-absorbent resin according to the present invention has a yellow index of 5.0 or less, which is whiter than a conventional resin, calculated in the measurement of yellow index (YI value) as described above. When an absorbent article, such as a diaper or a sanitary article, is manufactured using such a water-absorbent resin, the whiteness of its external appearance gives a clean impression to the user and can improve the commercial value as an absorbent article.

In addition, as described above, the water-absorbent resin according to the present invention has a yellow index of 5.0 or less and a yellow index change ratio ($\Delta$YI) after leaving for 10 days under 70° C. and 90% RH of 10 or less.

In general, if the water-absorbent resin in an absorbent article such as a sanitary napkin is discolored, the commercial value of the absorbent article decreases significantly. Accordingly, the water-absorbent resin to be applied to an absorbent article is required to be prevented from discoloring with passage of time, even if the resin is stored under a severe environment of high temperature and high humidity, such as the inside of a warehouse in summer.

In the water-absorbent resin according to the present invention, as described above, the water-absorption capacity of physiological saline is 55 g/g or more; the water-absorption capacity of physiological saline under a load of 4.14 kPa is 15 mL/g or more; the residual monomer content is 300 ppm or less; the yellow index is 5.0 or less; and the yellow index change ratio ($\Delta$YI) after leaving for 10 days under 70° C. and 90% RH is 10 or less. That is, the water-absorbent resin according to the present invention shows high water-absorption capacity under both no load and load conditions and has a significantly reduced residual monomer content and is therefore prevented from discoloring before and after storage for a long time under high temperature and high humidity (70° C., 90% RH). The yellow index after storage for 10 days under 70° C. and 90% RH is preferably 8 or less, more preferably 6 or less, and further preferably 4 or less. The yellow index change ratio (ΔYI) after storage for 14 days under 70° C. and 90% RH is preferably 20 or less and more preferably 17 or less. Furthermore, the yellow index change ratio (ΔYI) after storage for 21 days under 70° C. and 90% RH is preferably 30 or less and more preferably 25 or less.

(C) Median Particle Diameter

The water-absorbent resin according to the present invention preferably has a median particle diameter of 100 to 600 μm. This water-absorbent resin preferably has a median particle diameter of 200 to 500 μm, more preferably 250 to 450 μm, and further preferably 300 to 400 μm. In the water-absorbent resin according to the present invention, the amount of coarse resin particles is relatively low by forming the median particle diameter within a range of 100 to 600 μm, and the formative property of an absorbent material such as a hygienic material, for example, a diaper is high. Accordingly, the water-absorbent resin can be suitably used as a hygienic material, for example. In addition, the water-absorbent resin satisfying such a numerical range can prevent, for example, a reduction of agglomeration strength of secondary particles and a reduction in the absorption rate.

The particles of the water-absorbent resin may be in a single-particle state or an agglomerated state (secondary particles) of smaller particles (primary particles). Examples of the shape of the primary particle include substantially spherical, irregularly pulverized, and plate shapes. When primary particles are manufactured by reversed-phase suspension polymerization, the particles have, for example, a substantially spherical single particle shape having a smooth surface, such as a spherical or oval spherical shape. In the primary particles in such shapes, the surface shape is smooth, which gives enhanced flowability as a powder and also allows the agglomerated particles to be easily densely packed. Consequently, the water-absorbent resin, even if receives a shock, is scarcely broken and has high particle strength.

The water-absorption capacity of physiological saline, the water-absorption capacity of physiological saline under a load of 4.14 kPa, residual monomer content, yellow index (discoloration test), and median particle diameter of the above-described water-absorbent resin can all be measured by the methods described in Examples below.

In order to impart various properties to the resulting water-absorbent resin, an additive correspondent to the purpose may be blended to provide a water-absorbent resin composition. Examples of such an additive include inorganic powders, surfactants, oxidizing agents, reducing agents, radical chain inhibitors, antioxidants, antibacterial agents, and deodorants. For example, the flowability of a water-absorbent resin can be enhanced by adding 0.05 to 5 parts by mass of amorphous silica as an inorganic powder to 100 parts by mass of the water-absorbent resin.

2. Method of Producing Water-Absorbent Resin

The water-absorbent resin according to the present invention can be manufactured by polymerizing a water-soluble ethylenically unsaturated monomer in the presence of an internal-crosslinking agent.

The polymerization of a water-soluble ethylenically unsaturated monomer is performed by a typical polymerization method, such as aqueous solution polymerization, emulsion polymerization, or reversed-phase suspension polymerization. The aqueous solution polymerization is performed by heating an aqueous solution of a water-soluble ethylenically unsaturated monomer with stirring as necessary. The reversed-phase suspension polymerization is performed by heating a water-soluble ethylenically unsaturated monomer with stirring in a hydrocarbon dispersion medium. In the present invention, from the viewpoint of being able to strictly control the polymerization reaction and widely control the particle diameter, the reversed-phase suspension polymerization is preferred.

Regarding the water-absorbent resin according to the present invention, an example of the producing method will be described below.

A method of producing a water-absorbent resin by reversed-phase suspension polymerization of a water-soluble ethylenically unsaturated monomer in a hydrocarbon dispersion medium as an example of the method of producing the water-absorbent resin according to the present invention comprises, for concrete example, a step of performing the polymerization in the presence of an internal-crosslinking agent and in the presence of at least an azo-based compound and a peroxide, and a step of post-crosslinking the hydrous gel product having an internal-crosslinking structure obtained by the polymerization with a post-crosslinking agent.

<Polymerization Step>

[Water-Soluble Ethylenically Unsaturated Monomer]

Water-soluble ethylenically unsaturated monomers include, for example, (meth)acrylic acid ("(meth)acry" herein refers to both "acry" and "methacry". The same shall apply hereinafter) and salts thereof; 2-(meth)acrylamide-2-methylpropanesulfonic acid and salts thereof; nonionic monomers such as (meth)acrylamide, N,N-dimethyl(meth)acrylamide, 2-hydroxyethyl(meth)acrylate, N-methylol (meth)acrylamide, polyethylene glycol mono(meth)acrylate; amino group-containing unsaturated monomers such as N,N-diethylaminoethyl(meth)acrylate, N,N-diethylaminopropyl(meth)acrylate, diethylaminopropyl(meth)acrylamide and quaternary compounds thereof. Among these water-soluble ethylenically unsaturated monomers, (meth)acrylic acid or salts thereof, (meth)acrylamide, N,N-dimethylacrylamide are preferred in view of easy industrial availability, and (meth)acrylic acid and salts thereof are more preferred. Note that these water-soluble ethylenically unsaturated monomers may be used alone or in combination of two or more.

Among these monomers, acrylic acid and its salts are widely used as the raw materials for water-absorbent resins. These partially neutralized acrylic acid salts may also be copolymerized with another water-soluble ethylenically unsaturated monomer described above. In this case, the amount of the partially neutralized acrylic acid salts used as a main water-soluble ethylenically unsaturated monomer is preferably 70 to 100 mol % based on the total amount of the water-soluble ethylenically unsaturated monomers.

The water-soluble ethylenically unsaturated monomer in a form of an aqueous solution is dispersed in a hydrocarbon dispersion medium, and the dispersion is subjected to reversed-phase suspension polymerization. A water-soluble ethylenically unsaturated monomer in a form of an aqueous solution can increase the dispersion efficiency in a hydrocarbon dispersion medium. The concentration of the water-soluble ethylenically unsaturated monomer in the aqueous solution is preferably in a range from 20 mass % to the saturation concentration or less. Since the rate of polymerization in the presence of an azo compound tends to increase, from the viewpoint of avoiding excessive heat storage, the concentration of the monomer is preferably 55 mass % or less, more preferably 50 mass % or less, and further preferably 45 mass % or less. On the other hand, in order to maintain satisfactory productivity, the concentration of the monomer is preferably 25 mass % or more, more preferably 28 mass % or more, and further preferably 30 mass % or more.

When a water-soluble ethylenically unsaturated monomer has an acid group like as (meth)acrylic acid, 2-(meth) acrylamide-2-methylpropanesulfonic acid, those having the acid group pre-neutralized with an alkaline neutralizer may be used if desired. Such alkaline neutralizers include alkali metal salts such as sodium hydroxide, sodium carbonate, sodium hydrogen carbonate, potassium hydroxide, potassium carbonate; ammonia and the like. Further, these alkaline neutralizers may be used in the form of an aqueous solution in order to simply neutralization procedures. Note that the aforementioned alkaline neutralizers may be used alone or in combination of two or more.

The degree of neutralization of a water-soluble ethylenically unsaturated monomer with an alkaline neutralizer is generally preferably 10 to 100 mol % for all acid groups in the water-soluble ethylenically unsaturated monomer, more preferably 30 to 90 mol %, further preferably 40 to 85 mol %, and further more preferably 50 to 80 mol %, in order to enhance the water-absorption performance by increasing the osmotic pressure of the resulting water-absorbent resin and to prevent the occurrence of problems such as a problem in safety due to the presence of an excessive amount of an alkaline neutralizer.

[Internal-Crosslinking Agent]

Examples of the internal-crosslinking agent include internal-crosslinking agents that can crosslink the polymer of water-soluble ethylenically unsaturated monomers to be used, including, for example, unsaturated polyesters obtained by reacting a polyol including a diol and a triol such as (poly)ethylene glycol ("(poly)" refers to a case where a prefix "poly" exists and a case where the prefix does not exist. The same shall apply hereinafter.), (poly)propylene glycol, 1,4-butane diol, trimethylolpropane and (poly) glycerin, with an unsaturated acid such as (meth)acrylic acid, maleic acid and fumaric acid; bisacrylamides such as N,N-methylenebisacrylamide; di(meth)acrylic acid esters or tri(meth)acrylic acid esters obtained by allowing polyepoxide to react with (meth)acrylic acid; di(meth)acrylic acid carbamyl esters obtained by allowing polyisocyanate such as tolylene diisocyanate, hexamethylene diisocyanate to react with (meth)acrylic acid hydroxyethyl; compounds having two or more polymerizable unsaturated groups, for example, allylated starch, allylated cellulose, diallyl phthalate, N,N', N''-triallylisocyanate, divinylbenzene and the like; polyglycidyl compounds, for example, diglycidyl compounds such as (poly)ethylene glycol diglycidyl ether, (poly)propylene glycol diglycidyl ether, (poly)glycerin diglycidyl ether, triglycidyl compounds and the like; epihalohydrin compounds such as epichlorohydrin, epibromhydrin, α-methyl epichlorohydrin; compounds having two or more reactive functional groups, for example, isocyanate compounds such as 2,4-tolylene diisocyanate, hexamethylene diisocyanate; oxetane compounds such as 3-methyl-3-oxetane methanol, 3-ethyl-3-oxetane methanol, 3-butyl-3-oxetane methanol, 3-methyl-3-oxetane ethanol, 3-ethyl-3-oxetane ethanol, 3-butyl-3-oxetane ethanol. Among these internal-crosslinking agents, polyglycidyl compounds are preferably used, and diglycidyl compounds such as (poly)ethylene glycol diglycidyl ether, (poly)propylene glycol diglycidyl ether, (poly) glycerin diglycidyl ether are particularly preferably used. These internal-crosslinking agents may be used alone or in combination of two or more.

The used amount of the internal-crosslinking agent is preferably 0.000001 to 0.02 mol, more preferably 0.00001 to 0.01 mol, even more preferably 0.00001 to 0.005 mol, and still more preferably 0.00005 to 0.002 mol, based on 1 mol of the water-soluble ethylenically unsaturated monomer, from the viewpoint of reducing the water-soluble property by appropriate crosslinking in the resulting polymer to show sufficient water-absorption performance.

[Hydrocarbon Dispersion Medium]

Examples of the hydrocarbon dispersion medium include aliphatic hydrocarbons having 6 to 8 carbon atoms, such as n-hexane, n-heptane, 2-methylhexane, 3-methylhexane, 2,3-dimethylpentane, 3-ethylpentane, and n-octane; alicyclic hydrocarbons, such as cyclohexane, methylcyclohexane, cyclopentane, methylcyclopentane, trans-1,2-dimethylcyclopentane, cis-1,3-dimethylcyclopentane, and trans-1,3-dimethylcyclopentane; and aromatic hydrocarbons, such as benzene, toluene, and xylene. Among these hydrocarbon dispersion media, in particular, n-hexane, n-heptane, and cyclohexane are suitably used from the viewpoint of easy industrial availability, stable quality, and inexpensiveness. These hydrocarbon dispersion media may be used alone or in combination of two or more thereof. As examples of the mixture of hydrocarbon dispersion media, commercially available products, such as EXXSOL heptane (made by Exxon Mobil Corporation, hydrocarbon content: 75 to 85 mass % of heptane and its isomers), can also be used to give suitable results.

The used amount of the hydrocarbon dispersion medium is preferably 100 to 1500 parts by mass and more preferably 200 to 1400 parts by mass based on 100 parts by mass of the water-soluble ethylenically unsaturated monomer in the first stage, from the viewpoint of uniformly dispersing the water-soluble ethylenically unsaturated monomer and of easily controlling the polymerization temperature. Note that the reversed-phase suspension polymerization is performed in one stage (single stage) or multistage of two or more stages as described below. The above-described first-stage polymerization refers to single stage polymerization or the first-stage polymerization reaction in multistage polymerization (the same shall apply hereinafter).

[Dispersion Stabilizer]

(Surfactant)

In the reversed-phase suspension polymerization, in order to improve the dispersion stability of the water-soluble ethylenically unsaturated monomer in a hydrocarbon dispersion medium, a dispersion stabilizer may be used. The dispersion stabilizer can be a surfactant.

Usable examples of the surfactant include sucrose fatty acid esters, polyglycerin fatty acid esters, sorbitan fatty acid esters, polyoxyethylene sorbitan fatty acid esters, polyoxyethylene glycerine fatty acid esters, sorbitol fatty acid esters, polyoxyethylene sorbitol fatty acid esters, polyoxyethylene alkyl ethers, polyoxyethylene alkyl phenyl ethers, polyoxyethylene castor oil, polyoxyethylene hydrogenated castor oil, alkyl allyl formaldehyde condensed polyoxyethylene ethers, polyoxyethylene polyoxypropylene block copolymers, polyoxyethylene polyoxypropyl alkyl ethers, polyethylene glycol fatty acid esters, alkyl glucosides, N-alkyl gluconamides, polyoxyethylene fatty acid amides, polyoxyethylene alkylamines, phosphate esters of polyoxyethylene alkyl ethers, and phosphate esters of polyoxyethylene alkyl aryl ethers. Among these surfactants, in particular, sorbitan fatty acid esters, polyglycerin fatty acid esters, and sucrose fatty acid esters are preferably used in the viewpoint of dispersion stability of the monomer. These surfactants may be used alone or in combination of two or more thereof.

The used amount of the surfactant is preferably 0.1 to 30 parts by mass and more preferably 0.3 to 20 parts by mass based on 100 parts by mass of the water-soluble ethylenically unsaturated monomer in the first stage, in order to maintain the satisfactory dispersion state of the monomer in the hydrocarbon dispersion medium and achieve a dispersion effect corresponding to the used amount.

(Polymeric Dispersion Agent)

As the dispersion stabilizer to be used in the reversed-phase suspension polymerization, a polymeric dispersion agent may also be used together with the above-mentioned surfactant.

Examples of the polymeric dispersion agent include maleic anhydride modified polyethylenes, maleic anhydride modified polypropylenes, maleic anhydride modified ethylene-propylene copolymers, maleic anhydride modified ethylene-propylene-diene terpolymers (EPDMs), maleic anhydride modified polybutadienes, maleic anhydride-ethylene copolymers, maleic anhydride-propylene copolymers, maleic anhydride-ethylene-propylene copolymers, maleic anhydride-butadiene copolymers, polyethylenes, polypropylenes, ethylene-propylene copolymers, oxidized polyethylenes, oxidized polypropylenes, oxidized ethylene-propylene copolymers, ethylene-acrylic acid copolymers, ethyl cellulose, and ethyl hydroxyethyl cellulose. Among these polymeric dispersion agents, particularly preferred from the viewpoint of dispersion stability of the monomer are maleic anhydride modified polyethylenes, maleic anhydride modified polypropylenes, maleic anhydride modified ethylene-propylene copolymers, maleic anhydride-ethylene copolymers, maleic anhydride-propylene copolymers, maleic anhydride-ethylene-propylene copolymers, polyethylenes, polypropylenes, ethylene-propylene copolymers, oxidized polyethylenes, oxidized polypropylenes, and oxidized ethylene-propylene copolymers. These polymeric dispersion agents may be used alone or in combination of two or more thereof.

The used amount of the polymeric dispersion agent is preferably 0.1 to 30 parts by mass and more preferably 0.3 to 20 parts by mass based on 100 parts by mass of the water-soluble ethylenically unsaturated monomer in the first stage.

[Azo-Based Compound and Peroxide]

In an example of the method of producing a water-absorbent resin, an aqueous solution containing a water-soluble ethylenically unsaturated monomer is subjected to reversed-phase suspension polymerization in the presence of an azo-based compound and a peroxide.

In this polymerization step, the term "in the presence of an azo based compound and a peroxide" does not necessarily mean that the azo based compound and the peroxide are present in the solution at the time of starting the polymerization reaction, but means that when the monomer conversion ratio by radical cleavage of one of them is within 10 mol %, the other is also present in the solution. However, both of them are preferably present in the aqueous solution containing a monomer before the start of the polymerization reaction. The azo-based compound and the peroxide may be added to the polymerization reaction system via different flow channels or may be sequentially added to the polymerization reaction system via a single flow channel. Note that an azo-based compound and a peroxide to be used may be in the form of powder or an aqueous solution.

(Azo-Based Compound)

Azo-based compounds include, for example, those azo-based compounds such as 1-{(1-cyano-1-methylethyl)azo}formamide, 2,2'-azobis[2-(N-phenyl amidino)propane] dihydrochloride, 2,2'-azobis{2-[N-(4-chlorophenyl)amidino]propane} dihydrochloride, 2,2'-azobis{2-[N-(4-hydroxyphenyl)amidino]propane} dihydrochloride, 2,2'-azobis[2-(N-benzyl amidino)propane] dihydrochloride, 2,2'-azobis[2-(N-allyl amidino)propane] dihydrochloride, 2,2'-azobis(2-amidinopropane) dihydrochloride, 2,2'-azobis{2-[N-(2-hydroxyethyl)amidino]propane} dihydrochloride, 2,2'-azobis[2-(5-methyl-2-imidazoline-2-yl)propane] dihydrochloride, 2,2'-azobis[2-(2-imidazoline-2-yl)propane] dihydrochloride, 2,2'-azobis[2-(4,5,6,7-tetrahydro-1H-1,3-diazepine-2-yl)propane] dihydrochloride, 2,2'-azobis[2-(5-hydroxy-3,4,5,6-tetrahydro-pyrimidine-2-yl)propane] dihydrochloride, 2,2'-azobis{2-[1-(2-hydroxyethyl)-2-imidazoline-2-yl]propane} dihydrochloride, 2,2'-azobis[2-(2-imidazoline-2-yl)propane], 2,2'-azobis{2-methyl-N-[1,1-bis(hydroxymethyl)-2-hydroxyethyl]propionamide}, 2,2'-azobis{2-methyl-N-[1,1-bis(hydroxymethyl)ethyl]propionamide}, 2,2'-azobis[2-methyl-N-(2-hydroxyethyl)propionamide], 2,2'-azobis(2-methylpropionamide) dihydrochloride, 4,4'-azobis-4-cyanovaleinic acid, 2,2'-azobis[2-(hydroxymethyl)propionitrile], 2,2'-azobis[2-(2-imidazoline-2-yl)propane]disulfate dihydrate, 2,2'-azobis[N-(2-carboxyethyl)-2-methylpropionamidine] tetrahydrate, 2,2'-azobis[2-methyl-N-(2-hydroxyethyl)propionamide]. Among these compounds, preferred are 2,2'-azobis(2-amidinopropane) dihydrochloride, 2,2'-azobis{2-[1-(2-hydroxyethyl)-2-imidazoline-2-yl]propane} dihydrochloride, and 2,2'-azobis[N-(2-carboxyethyl)-2-methylpropionamidine] tetrahydrate. These azo compounds may be used alone or in combination of two or more.

(Peroxide)

Peroxides include, for example, persulfates such as potassium persulfate, ammonium persulfate, sodium persulfate; peroxides such as methyl ethyl ketone peroxide, methyl isobutyl ketone peroxide, di-t-butyl peroxide, t-butyl cumyl peroxide, t-butyl peroxyacetate, t-butyl peroxy isobutyrate, t-butyl peroxy pivalate, hydrogen peroxide. Among these peroxides, potassium persulfate, ammonium persulfate, sodium persulfate, and hydrogen peroxide are preferably used; and potassium persulfate, ammonium persulfate, and sodium persulfate are more preferably used. These peroxides may be used alone or in combination of two or more.

(Used Amount and Used Proportion of Azo-Based Compound and Peroxide)

The used amount of the azo-based compound and the peroxide is generally preferably 0.00005 mol or more, more preferably 0.0001 mol or more, based on 1 mol of the water-soluble ethylenically unsaturated monomer, from the viewpoint of reducing the time of the polymerization reaction. In addition, from the viewpoint of preventing a rapid polymerization reaction, the amount is preferably 0.005 mol or less, more preferably 0.001 mol or less, based on 1 mol of the water-soluble ethylenically unsaturated monomer.

The used proportion of the used amount of the azo-based compound to the total amount of the azo-based compound and the peroxide is preferably 40 mass % or more, more preferably 50 mass % or more, further preferably 60 mass % or more, and further more preferably 70 mass % or more. At the same time, the proportion of the used amount of the azo-based compound to the total amount of the azo-based compound and the peroxide is preferably 95 mass % or less, more preferably 90 mass % or less, further preferably 85 mass % or less, and further more preferably 80 mass % or less. The mass ratio range (azo-based compound:peroxide) is preferably from 8:12 to 19:1.

[Aminocarboxylic Acid Compound]

In the water-absorbent resin according to the present invention, it is desirable to further blend an aminocarboxylic acid compound in the resin.

Examples of the aminocarboxylic acid compound include aminocarboxylic acids, such as iminodiacetic acid, hydroxyethyliminodiacetic acid, nitrilotriacetic acid, nitrilotripropionic acid, ethylenediaminetetraacetic acid, diethylenetriaminepentaacetic acid, triethylenetetraminehexaacetic acid, trans-1,2-diaminocyclohexanetetraacetic acid, N,N-bis(2-hydroxyethyl)glycine, diaminopropanoltetraacetic acid, ethylenediaminedipropionic acid, hydroxyethylenediaminetriacetic acid, glycol ether diaminetetraacetic acid, diaminopropanetetraacetic acid, N,N'-bis(2-hydroxybenzyl) ethylenediamine-N,N'-diacetic acid, and 1,6-hexamethylenediamine-N,N,N',N'-tetraacetic acid; and salts thereof. Among these compounds, diethylenetriaminepentaacetic acid, triethylenetetraminehexaacetic acid, trans-1,2-diaminocyclohexanetetraacetic acid, ethylenediaminetetraacetic acid, and salts thereof are more suitably used, from the viewpoint of further reducing the yellow index change ratio of the water-absorbent resin. These aminocarboxylic acid compounds may be used alone or in combination of two or more thereof.

Examples of the method of blending the aminocarboxylic acid compound in the water-absorbent resin include (1) a method by addition to an aqueous solution of the water-soluble ethylenically unsaturated monomer before polymerization, (2) a method by addition to the resulting hydrous gel product after polymerization, (3) a method by addition to the water-absorbent resin during drying, (4) a method by powder mixing with the water-absorbent resin after drying, and (5) a method by addition to the water-absorbent resin dispersed in an organic solvent and then heating for removal of the solvent.

In blending of the aminocarboxylic acid compound, in order to uniformly disperse the aminocarboxylic acid compound in the water-absorbent resin, preferred is addition of a solution prepared by dissolving the aminocarboxylic acid compound of a liquid or powder form in a hydrophilic solvent such as water or addition of the aminocarboxylic acid compound in a powder form.

The amount of the aminocarboxylic acid compound to be blended is preferably 0.001 to 10 parts by mass based on 100 parts by mass of the water-soluble ethylenically unsaturated monomer, more preferably 0.005 to 5 parts by mass, further preferably 0.01 to 3 parts by mass, and further more preferably 0.05 to 2 parts by mass.

[Other Components]

In the method of producing the water-absorbent resin, other components may be added to an aqueous solution containing a water-soluble ethylenically unsaturated monomer to perform reversed-phase suspension polymerization if desired. As other components, chain transfer agents, thickener, other various additives and the like may be added.

(Chain Transfer Agent)

Specifically, in the method of producing the water-absorbent resin, in order to control the water-absorption performance of the water-absorbent resin, the water-soluble ethylenically unsaturated monomer may be polymerized in the presence of a chain transfer agent.

Examples of the chain transfer agent include: thiols such as ethane thiol, propane thiol and dodecanethiol; thiol acids such as thioglycolic acid, thiomalic acid, dimethyl dithiocarbamate, diethyl dithiocarbamate and salts thereof; secondary alcohols such as isopropanol; phosphorous acid compounds, such as normal salts of phosphorous acid (for example, as phosphorous acid, phosphorous acid disodium, dipotassium phosphite and phosphorous acid diammonium, etc.), and such as acidic salts of phosphorous acid (for example, as sodium hydrogen phosphite, potassium hydrogen phosphite and phosphorous acid ammonium hydrogen, etc.); phosphoric acid compounds, such as normal salts of phosphoric acid (for example, as phosphoric acid, sodium phosphate, potassium phosphate and ammonium phosphate, etc.), and such as acid salts of phosphoric acid (for example, as sodium dihydrogen phosphate, potassium dihydrogen phosphate, ammonium dihydrogen phosphate, disodium hydrogen phosphate, potassium hydrogen phosphate dibasic and diammonium hydrogen phosphate, etc.); hypophosphorous acid compounds such as hypophosphorous acid salts (for example, as hypophosphorous acid, sodium hypophosphite, potassium hypophosphite and ammonium hypophosphite, etc.); pyrophosphoric acid, tripolyphosphate, polyphosphoric acid and the salts thereof; and trimethyl phosphate, nitrilotrimethylene triphosphonic acid and the like. These chain transfer agents may be used alone or in combination of two or more. As the chain transfer agent, the hydrate thereof may be used.

The used amount of chain transfer agent is preferably 0.00001 to 0.0005 mol, more preferably 0.000025 to 0.00012 mol, based on 1 mol of the water-soluble ethylenically unsaturated monomer. A used amount of the chain transfer agent of less than 0.00001 mol based on 1 mol of the water-soluble ethylenically unsaturated monomer tends not to provide a water-absorbent resin having high water-absorption capacity and high gel strength. In contrast, a used amount of higher than 0.0005 mol tends not to provide an effect corresponding to the amount used.

(Thickener)

In the method of producing the water-absorbent resin, the reversed-phase suspension polymerization may be performed by adding a thickener to an aqueous solution containing a water-soluble ethylenically unsaturated monomer. The median particle diameter obtained by reversed-phase suspension polymerization can be controlled by adjusting the viscosity of the aqueous solution by addition of a thickener.

Specifically, as a thickener, for example, hydroxyethyl cellulose, hydroxypropyl cellulose, methyl cellulose, carboxymethyl cellulose, polyacrylic acid, (partially) neutralized polyacrylic acid, polyethylene glycol, polyacrylamide, polyethyleneimine, dextrin, sodium alginate, polyvinyl alcohol, polyvinyl pyrrolidone, polyethylene oxide and the like can be used. Note that in a case where the stirring speeds at the time of polymerization are the same, there is a tendency that the higher the viscosity of an aqueous solution of a water-soluble ethylenically unsaturated monomer is, the larger the median particle diameter of the resulting particles is.

[Reversed-Phase Suspension Polymerization]

When performing reversed-phase suspension polymerization, for example, an aqueous monomer solution containing a water-soluble ethylenically unsaturated monomer is dispersed in a hydrocarbon dispersion medium in the presence of a surfactant and/or a polymeric dispersion agent. On this occasion, the time of adding a surfactant and a polymeric dispersion agent may be either before or after the addition of the aqueous monomer solution as long as they are added before the start of the polymerization reaction.

In particular, in a view of easy reduction of the amount of a residual hydrocarbon dispersion medium in the resulting water-absorbent resin, it is preferred that polymerization is performed after an aqueous monomer solution is added and then dispersed in a hydrocarbon dispersion medium in which a polymeric dispersion agent has been dispersed, and then a surfactant is further dispersed.

Such reversed-phase suspension polymerization can be performed by a single stage or multistage of two or more stages. In addition, from the viewpoint of increasing productivity, polymerization by two or three stages is more preferred.

In the case of multistage reversed-phase suspension polymerization by two or more stages, the first-stage reversed-phase suspension polymerization is performed, and a water-soluble ethylenically unsaturated monomer is then added to and mixed with the reaction mixture obtained by the first-stage polymerization reaction to perform second-stage reversed-phase suspension polymerization as in the first-stage. In the reversed-phase suspension polymerization in the second and subsequent stages, the reversed-phase suspension polymerization is preferably performed by adding, in addition to the water-soluble ethylenically unsaturated monomer, an internal-crosslinking agent and the above-described azo compound and peroxide to the water-soluble ethylenically unsaturated monomer within the above-mentioned molar ratio ranges based on the amount of the water-soluble ethylenically unsaturated monomer to be added in the reversed-phase suspension polymerization in each stage of the second and subsequent stages.

For the reaction temperature for a polymerization reaction, it is preferably 20 to 110° C., more preferably 40 to 90° C. from the viewpoint that profitability may be improved by allowing prompt progress of a polymerization to reduce a polymerization time, and polymerization heat may be easily removed to perform a smooth reaction. Further, the reaction time is preferably 0.5 to 4 hours.

<Post-Crosslinking Step>

The hydrous gel product having an internal-crosslinking structure prepared by polymerization of the water-soluble ethylenically unsaturated monomer is then post-crosslinked (post-crosslinking reaction) with a post-crosslinking agent to obtain the water-absorbent resin according to the present invention. This post-crosslinking reaction is preferably performed in the presence of the post-crosslinking agent after the polymerization of the water-soluble ethylenically unsaturated monomer. By thus performing the post-crosslinking reaction of the hydrous gel product having an internal-crosslinking structure after the polymerization, the crosslinking density can be increased in the vicinity of the surface of the water-absorbent resin and can enhance various properties, such as water-absorption capacity under both no load and load condition.

Specifically, post-crosslinking agents can include, those compounds having two or more reactive functional groups. They include, for example, polyols such as ethylene glycol, propylene glycol, 1,4-butanediol, trimethylolpropane, glycerin, polyoxyethylene glycol, polyoxypropylene glycol, polyglycerin; polyglycidyl compounds such as (poly)ethylene glycol diglycidyl ether, (poly)glycerin diglycidyl ether, (poly)glycerin triglycidyl ether, trimethylolpropane triglycidyl ether, (poly)propylene glycol polyglycidyl ether, (poly)glycerol polyglycidyl ether; haloepoxy compounds such as epichlorohydrin, epibromhydrin, α-methyl epichlorohydrin; isocyanate compounds such as 2,4-tolylene diisocyanate, hexamethylene diisocyanate; oxetane compounds such as 3-methyl-3-oxetane methanol, 3-ethyl-3-oxetane methanol, 3-butyl-3-oxetane methanol, 3-methyl-3-oxetane ethanol, 3-ethyl-3-oxetane ethanol, 3-butyl-3-oxetane ethanol; oxazoline compounds such as 1,2-ethylenebisoxazoline; carbonate compounds such as ethylene carbonate; hydroxyalkylamide compounds such as bis[N,N-di((β-hydroxyethyl)]adipamide. Among these post-crosslinking agents, particularly preferred are polyglycidyl compounds such as (poly)ethylene glycol diglycidyl ether, (poly)glycerin diglycidyl ether, (poly)glycerol triglycidyl ether, trimethylolpropane triglycidyl ether, (poly)propylene glycol polyglycidyl ether, (poly)glycerol polyglycidyl ether. These post-crosslinking agents may be used alone or in combination of two or more.

The used amount of the post-crosslinking agent is preferably 0.00001 to 0.01 mol based on 1 mol of the total amount of the water-soluble ethylenically unsaturated monomer used for the polymerization, more preferably 0.00005 to 0.005 mol, and even more preferably 0.0001 to 0.002 mol. The used amount of the post-crosslinking agent is preferably 0.00001 mol or more from the viewpoint of sufficiently increasing the crosslinking density of the surface of the water-absorbent resin and is preferably 0.01 mol or less from the viewpoint of increasing the water-absorption capacity of the water-absorbent resin.

As a method of adding a post-crosslinking agent, the post-crosslinking agent may be added as it is or as an aqueous solution. A post-crosslinking agent may also be added as a solution in which a hydrophilic organic solvent is used as a solvent if desired. Hydrophilic organic solvents include, for example, lower alcohols such as methyl alcohol, ethyl alcohol, n-propyl alcohol, isopropyl alcohol; ketones such as acetone, methyl ethyl ketone; ethers such as diethyl ether, dioxane, tetrahydrofuran; amides such as N,N-dimethylformamide; sulfoxides such as dimethyl sulfoxide. These hydrophilic organic solvents may be used alone or in combination of two or more, or may be used as a mixed solvent with water.

The post-crosslinking agent may be added after the polymerization reaction of the water-soluble ethylenically unsaturated monomer has been almost completed, and is preferably added in the presence of water in a range of 1 to 400 parts by mass based on 100 parts by mass of the water-soluble ethylenically unsaturated monomer, more preferably in a range of 5 to 200 parts by mass, further preferably in a range of 10 to 100 parts by mass, and further more preferably in a range of 20 to 60 parts by mass. This can, for example, enhance the water-absorption capacity under a load. Note that the amount of water means the sum of the amount of water in a polymerization reaction system and the amount of water used as necessary on the occasion of adding a post-crosslinking agent.

The reaction temperature of the post-crosslinking reaction is preferably 50° C. to 250° C., more preferably 60° C. to 180° C., further preferably 60° C. to 140° C., and further more preferably 70° C. to 120° C. The time for the post-crosslinking reaction is preferably 1 to 300 minutes and more preferably 5 to 200 minutes.

<Drying Step>

A drying step of removing water, a hydrocarbon dispersion medium and the like using distillation by applying energy such as heat from the outside after performing the aforementioned reversed phase suspension polymerization may be included. When performing dehydration of a hydrous gel after reversed phase suspension polymerization, a system in which the hydrous gel is dispersed in a hydrocarbon dispersion medium is heated to temporarily evaporate water and the hydrocarbon dispersion medium from the system by azeotropic distillation. At this time, only the hydrocarbon dispersion medium evaporated is allowed to return into the system, enabling continuous azeotropic distillation. In that case, the temperature in the system during the drying treatment is maintained at or below the azeotropic temperature of the hydrocarbon dispersion medium. Therefore this is preferred from the view point that, for example, the resin is less susceptible to deterioration. Water and the hydrocarbon dispersion medium is continuously evaporated away to obtain particles of a water-absorbent resin. By controlling processing conditions of this drying step after polymerization to adjust the amount of dehydrated water, various properties of the resulting water-absorbent resin can be controlled.

In the drying step, the drying treatment may be performed by distillation under an ordinary pressure or under a reduced pressure. In addition, the drying treatment may be performed in a flow of gas such as nitrogen, from the viewpoint of increasing the drying efficiency. When the drying treatment is performed under an ordinary pressure, the drying temperature is preferably 70° C. to 250° C., more preferably 80° C. to 180° C., further preferably 80° C. to 140° C., and further more preferably 90° C. to 130° C. When the drying treatment is performed under a reduced pressure, the drying temperature is preferably 40° C. to 160° C. and more preferably 50° C. to 110° C.

When the post-crosslinking step is performed with a post-crosslinking agent after reversed-phase suspension polymerization of a monomer, the above-described drying step by distillation is performed after the completion of the post-crosslinking step. Alternatively, the post-crosslinking step and the drying step may be performed simultaneously.

In addition, various additives, such as a reducing agent, an oxidizing agent, an antibacterial agent, and a deodorant, are optionally added to the water-absorbent resin after the polymerization step and during or after the drying step.

3. Absorbent Material and Absorbent Article

The water-absorbent resin of the present invention has characteristics, as described above, (A) a water-absorption capacity of physiological saline of 55 g/g or more, a water-absorption capacity of physiological saline under a load of 4.14 kPa of 15 mL/g or more, and a residual monomer content of 300 ppm or less; and (B) a yellow index of 5.0 or less and a yellow index change ratio ($\Delta YI$) after leaving for 10 days under 70° C. and 90% RH of 10 or less. Accordingly, the water-absorbent resin can be suitably used as a hygienic material that is applied to a sanitary article, a disposable diaper, or the like, for example.

Here, an absorbent material including the water-absorbent resin is composed of, for example, the water-absorbent resin and a hydrophilic fiber. Examples of the structure of the absorbent material include, but are not limited to, a dispersion mixture prepared by mixing a water-absorbent resin and a hydrophilic fiber to give a uniform composition; a sandwich structure including a water-absorbent resin disposed between layered hydrophilic fibers; and a structure including a water-absorbent resin and a hydrophilic fiber wrapped by tissue. In addition, the absorbent material may further include other components, for example, an adhesive binder, such as a thermal adhesive synthetic fiber, a hot melt adhesive, or an adhesive emulsion, for enhancing the shape retention property of the absorbent material.

The content of the water-absorbent resin in the absorbent material is preferably 25 to 98 mass %, more preferably 35 to 95 mass %, and even more preferably 45 to 90 mass %, from the viewpoint of being suitably used in thinner products including smaller amounts of hydrophilic fibers, etc. than conventional products. If the content of the water-absorbent resin is less than 25 mass %, the absorbent material has a reduced absorption volume and thereby has a possibility of causing liquid leakage or re-wet of a liquid. In contrast, if the content of the water-absorbent resin is higher than 98 mass %, the cost of the absorbent material increases, and the feeling of the absorbent material becomes harder.

Hydrophilic fibers include cellulose fibers such as cotton-like pulp obtained from wood, mechanical pulp, chemical pulp, semichemical pulp; artificial cellulose fibers such as rayon, acetate; fibers comprising synthetic resin such as hydrophilized polyamide, polyester, and polyolefine.

Moreover, an absorbent material in which a water-absorbent resin is used can be held between a liquid permeable sheet (top sheet) through which a liquid can permeate and a liquid impermeable sheet (back sheet) through which a liquid cannot permeate to give an absorbent article. The liquid permeable sheet is arranged on the side to be in contact with the body while the liquid impermeable sheet is arranged opposite to the side to be in contact with the body.

Liquid permeable sheets include non-woven of an air through type, a span bond type, a chemical bond type, a needle punch type and the like comprising fiber such as polyethylene, polypropylene, polyester, etc. and porous synthetic resin sheets and the like. Further, liquid impermeable sheets include synthetic resin films comprising a resin such as polyethylene, polypropylene, polyvinyl chloride and the like.

Typical examples of the absorbent article include hygienic materials, such as disposable diapers, sanitary napkins, and incontinence pads; urine-absorbent materials for pets; materials for civil engineering and construction, such as packing materials; materials for keeping food freshness, such as drip absorbents and refrigerants; and agricultural and horticultural articles, such as water retaining materials for soil.

EXAMPLES

4. Example

Hereafter, the present invention will be described in detail with reference to Examples and Comparative Examples. However, the present invention shall not in any way be limited to the following Examples and the like.

4-1. Method of Evaluation Test

The water-absorbent resins prepared by the following Examples and Comparative Examples were evaluated by various tests described below. The method of each evaluation test will be described below.

(1) Water-Absorption Capacity of Physiological Saline

In a 500 mL beaker, 500 g of an aqueous 0.9 mass % sodium chloride solution (physiological saline) was weighed, and 2.0 g of a water-absorbent resin was dispersed therein with stirring at 600 r/min so as to prevent generation of lumps. The mixture was left to stand for 60 minutes in the stirred state to sufficiently swell the water-absorbent resin. The mass Wa (g) of a standard sieve with openings of 75 μm was measured in advance, and the content in the beaker was filtered through this sieve. The sieve was tilted to form an angle of about 30 degrees with respect to the horizontal and was left to stand in this state for 30 minutes to filter out excessive water. The mass Wb (g) of the sieve containing the water-absorbed gel was measured, and the water-absorption capacity of physiological saline was determined by the following formula.

Water-absorption capacity of physiological saline $(g/g)=[Wb-Wa]$ (g)/mass (g) of water-absorbent resin (2) Water-Absorption Capacity of Physiological Saline Under a Load of 4.14 kPa A water-absorption capacity of physiological saline under a load of 4.14 kPa of a water-absorbent resin was measured using a measurement apparatus X. A schematic arrangement of the measurement apparatus X is shown in FIG. 1.

The measurement apparatus X shown in FIG. 1 comprises a buret part 1, a conduit 2, a measurement stage 3, a measurement part 4 placed on the measurement stage 3. In the buret part 1, a rubber stopper 14 is connected to the upper part of a buret 10, and an air introducing tube 11 and a cock 12 is connected to the lower part of the buret 10. Further, a cock 13 is attached to the upper part of the air introducing tube 11. A conduit 2 connects the buret part 1 and the measurement stage 3. The diameter of the conduit 2 is 6 mm. The measurement stage 3 has a hole with a diameter of 2 mm at the center, to which the conduit 2 is connected. The measurement part 4 is provided with a cylinder 40 and a nylon mesh 41 patched on the bottom of the cylinder 40, as well as a weight 42. The inner diameter of the cylinder 40 is 2.0 cm. The nylon mesh 41 is formed as 200 mesh (75 μm openings). Further, it is configured such that a predetermined amount of a water-absorbent resin 5 is uniformly distributed on the nylon mesh 41. The weight 42 has a diameter of 1.9 cm and a mass of 119.6 g. The weight 42 is to be placed on the water-absorbent resin 5 to uniformly apply a load of 4.14 kPa to the water-absorbent resin 5.

Using the measurement apparatus X having a structure as described above, first, the cock 12 and the cock 13 at the buret part 1 were closed, and then physiological saline adjusted to 25° C. was introduced into the buret 10 from the top. Subsequently, the top of the buret was plugged with the rubber stopper 14, and then the cock 12 and the cock 13 at the buret part 1 were opened. Next, the height of the measurement stage 3 was adjusted so that the tip of the conduit 2 at the center of the measurement stage 3 is leveled with the air inlet of the air introducing tube 11.

Meanwhile, 0.10 g of the water-absorbent resin 5 was uniformly distributed on the nylon mesh 41 in the cylinder 40, and then the weight 42 was placed on that water-absorbent resin 5. The measurement part 4 was arranged so that its center coincided with the conduit inlet at the center of the measurement stage 3.

The amount of reduced physiological saline in the buret 10 (the amount of physiological saline absorbed by the water-absorbent resin 5) Wa (mL) was continuously measured from the time point when the water-absorbent resin 5 started to absorb water. At an elapsed time of 60 minutes from the start of water absorption, a water-absorption capacity of physiological saline under a load of 4.14 kPa of the water-absorbent resin was calculated by the following formula.

Water-absorption capacity of physiological saline under a load of 4.14 kPa (mL/g)=Wc/0.10 (g).

(3) Residual Monomer Content (Residual Monomer Content in Water-Absorbent Resin)

In a 500 mL beaker, 500 g of physiological saline was placed, and 2.0 g of a water-absorbent resin was added thereto, followed by stirring for 60 minutes. The content in the beaker was filtered through a JIS standard sieve with openings of 75 μm and then through a filter paper (made by ADVANTEC MFS, Inc., Filter Paper No. 3) to separate the water-absorbed gel from the extract. The content of the monomer dissolved in the resulting extract was measured by high-performance liquid chromatography. The measured value was converted into the value per mass of the water-absorbent resin particles to determine the residual monomer content (ppm).

The high-performance liquid chromatography was performed under the following conditions:

Model: SCL-10AVP+CTO-10A+LC-10AD+DGU-4A+SIL-10A, made by Shimadzu Corporation,

Detector: SPD-10A (UV wavelength: 210 nm), made by Shimadzu Corporation,

Column: Shodex KC-811, made by Showa Denko K.K.,

Column temperature: 45° C., and

Carrier: Distilled water adjusted to pH 2 with phosphoric acid.

(4) Median Particle Diameter

As a lubricant, 0.25 g of amorphous silica (Carplex #80, made by Evonik Degussa Japan, Inc.) was mixed with 50 g of a water-absorbent resin. The mixture was allowed to pass through a JIS standard sieve with openings of 250 μm. When the residual amount on the sieve was 50 mass % or more of the mixture, the median particle diameter was measured using the following combination [A] of sieves. When the residual amount was less than 50 mass %, the median particle diameter was measured using the following combination [B] of sieves.

Combination [A] of JIS standard sieves: a sieve of 850 μm openings, a sieve of 600 μm openings, a sieve of 500 μm openings, a sieve of 400 μm openings, a sieve of 300 μm openings, a sieve of 250 μm openings, and a sieve of 150 μm openings, and a receiving tray, in this order from the top.

Combination [B] of JIS standard sieves: a sieve of 400 μm openings, a sieve of 250 μm openings, a sieve of 180 μm openings, a sieve of 150 μm openings, a sieve of 106 μm openings, a sieve of 75 μm openings, and a sieve of 45 μm openings, and a receiving tray, in this order from the top.

The water-absorbent resin was placed in the sieve at the top of the combination of sieves, followed by classification by shaking with a low-tap shaker for 20 minutes. After the classification, the mass of the water-absorbent resin remaining on each sieve was calculated as the mass proportion based on the total mass. By integrating the masses in order of decreasing particle diameter, the relationship between the sieve openings and the integrated value of the mass proportion of the water-absorbent resin remaining in the sieves was plotted on logarithmic probability paper. The plots on the probability paper were connected with a straight line to determine the particle diameter corresponding to 50 mass % in the integrated mass proportion as the median particle diameter.

(5) Yellow Index and Yellow Index Change Ratio of Water-Absorbent Resin (Discoloration Test)

In a glass measurement container with an inner diameter of 3 cm, 2.0 g of a water-absorbent resin was placed. The yellow index of the water-absorbent resin was measured with a color difference meter (Color Meter ZE2000, made by Nippon Denshoku Industries Co., Ltd.) of which the tristimulus values, X, Y, and Z, were corrected with a white sheet for calibration. The yellow index was calculated as the initial value from the resulting tristimulus values, X, Y, and Z of the water-absorbent resin by the following formula:

Yellow index=$100(1.28X-1.06Z)/Y$

Discoloration of the water-absorbent resin with passage of time was tested as follows. That is, 2.0 g of a water-absorbent resin was uniformly placed in a polypropylene container having an inner diameter of 3 cm and a depth of 1 cm, and the container was stored in a desktop constant temperature and humidity chamber set to a temperature of 70° C.±2° C. and a relative humidity of 90%±2% RH for a predetermined number of days. After passage of the predetermined number of days, the container was taken out from the constant temperature and humidity chamber and was left to stand for a while to cool until room temperature. The whole amount of the water-absorbent resin in the container was placed in a glass measurement container having an inner diameter of 3 cm, and the yellow index of the water-absorbent resin was measured with a color difference meter (Color Meter ZE2000, made by Nippon Denshoku Industries Co., Ltd.). The yellow index was calculated from the resulting tristimulus values, X, Y, and Z, of the water-absorbent resin by the following formula. The yellow index was measured for the water-absorbent resins stored for 7 days, for 10 days, for 14 days, and for 21 days in the constant temperature and humidity chamber to examine the discoloration of the water-absorbent resin with passage of time.

Yellow index=$100(1.28X-1.06Z)/Y$

The yellow index change ratio ($\Delta$YI) of the water-absorbent resin is calculated as the change ratio in the yellow index after the storage under 70° C. and 90% RH for a predetermined number of days by the following formula:

Yellow index change ratio ($\Delta$YI)=[(yellow index after storage for a predetermined number of days)−(yellow index before the storage)]/(yellow index before the storage)

4-2. Examples and Comparative Examples

Example 1

A 2-L cylindrical round-bottom separable flask having an inner diameter of 110 mm and equipped with a reflux condenser, a dropping funnel, a nitrogen gas-introducing tube, and stirrer having stirring blades compound of two sets of 4 inclined paddle blades with a blade diameter of 50 mm was prepared. Into this flask added were 300 g of n-heptane, 0.74 g of sucrose stearic acid ester of HLB3 (made by Mitsubishi-Kagaku Foods Corporation, Ryoto sugar ester S-370) as a surfactant, and 0.74 g of maleic anhydride modified ethylene-propylene copolymer (made by Mitsui Chemicals, Inc., High Wax 1105A) as a polymeric dispersion agent. The mixture was heated to 80° C. with stirring to dissolve the surfactant and was then cooled to 50° C.

Meanwhile, 92 g (1.02 mol) of an aqueous 80 mass % acrylic acid solution was put in a 500-mL Erlenmeyer flask, and 146.0 g of an aqueous 21 mass % sodium hydroxide solution was dropwise added thereto while cooling from the outside for neutralization at 75 mol %. Subsequently, 0.092 g of hydroxyethyl cellulose (made by Sumitomo Seika Chemicals Co., Ltd., HEC AW-15F) as a thickener, 0.092 g (0.339 mmol) of 2,2'-azobis(2-amidinopropane) dihydrochloride as an azo-based compound, 0.041 g (0.172 mmol) of sodium persulfate as a peroxide, and 0.01012 g (0.058 mmol) of ethylene glycol diglycidyl ether as an internal-crosslinking agent were added thereto and dissolved to prepare an aqueous monomer solution.

The aqueous monomer solution prepared as described above was added to the separable flask, and the atmosphere in the system was thoroughly replaced with nitrogen. The flask was then immersed in a 70° C. water bath to raise the temperature to perform polymerization for 60 minutes to prepare a first-stage polymerized slurry.

Meanwhile, 128.8 g (1.43 mol) of an aqueous 80 mass % acrylic acid solution was put in another 500-mL Erlenmeyer flask, and 159.0 g of an aqueous 27 mass % sodium hydroxide solution was dropwise added thereto while cooling from the outside for neutralization at 75 mol %. Subsequently, 0.129 g (0.475 mmol) of 2,2'-azobis(2-amidinopropane) dihydrochloride as an azo-based compound, 0.058 g (0.244 mmol) of sodium persulfate as a peroxide, and 0.0116 g (0.067 mmol) of ethylene glycol diglycidyl ether as an internal-crosslinking agent were added thereto and dissolved to prepare a second-stage aqueous monomer solution.

The inside of the above-described separable flask system was cooled to 25° C., and the whole quantity of the second-stage aqueous monomer solution was then added to the first-stage polymerized slurry. The atmosphere in the system was thoroughly replaced with nitrogen, and the flask was then immersed in a 70° C. water bath again to raise the temperature to perform second-stage polymerization for 30 minutes.

After the second-stage polymerization, the temperature of the reaction solution was raised with a 125° C. oil bath, and 240 g of water was removed to the outside of the system by azeotropic distillation of n-heptane and water while refluxing n-heptane. Subsequently, 4.42 g (0.51 mmol) of an aqueous 2 mass % ethylene glycol diglycidyl ether solution was added thereto as a post-crosslinking agent, and the mixture was maintained at 80° C. for 2 hours. Subsequently, drying step was performed by evaporating the n-heptane to obtain a dried resin. This dried resin was allowed to pass through a sieve with openings of 1000 μm to obtain 231.4 g of a water-absorbent resin in a form of agglomerated spherical particles. The thus-prepared water-absorbent resin was evaluated in accordance with each type of the above-described test methods. The resulting water-absorbent resin had a median particle diameter of 380 μm.

Example 2

Example 2 was performed as in Example 1 except that 0.058 g (0.215 mmol) of potassium persulfate was dissolved in the first-stage aqueous monomer solution as the peroxide and that 0.081 g (0.300 mmol) of potassium peroxide was dissolved in the second-stage aqueous monomer solution as the peroxide. The thus-prepared 231.8 g of water-absorbent resin was evaluated in accordance with each type of the above-described test methods. The resulting water-absorbent resin had a median particle diameter of 365 μm.

Example 3

A 2-L cylindrical round-bottom separable flask having an inner diameter of 110 mm and equipped with a reflux condenser, a dropping funnel, a nitrogen gas-introducing tube, and stirrer having stirring blades compound of two sets of 4 inclined paddle blades with a blade diameter of 50 mm was prepared. Into this flask added were 300 g of n-heptane, 0.74 g of HLB3 sucrose stearic acid ester (made by Mitsubishi-Kagaku Foods Corporation, Ryoto sugar ester S-370) as a surfactant, and 0.74 g of maleic anhydride modified ethylene-propylene copolymer (made by Mitsui Chemicals, Inc., High Wax 1105A) as a polymeric dispersion agent. The mixture was heated to 80° C. with stirring to dissolve the surfactant and was then cooled to 50° C.

Meanwhile, 92 g (1.02 mol) of an aqueous 80 mass % acrylic acid solution was put in a 500-mL Erlenmeyer flask, and 146.0 g of an aqueous 21 mass % sodium hydroxide solution was dropwise added thereto while cooling from the outside for neutralization at 75 mol %. Subsequently, 0.092 g of hydroxylethyl cellulose (made by Sumitomo Seika Chemicals Co., Ltd., HEC AW-15F) as a thickener, 0.092 g (0.339 mmol) of 2,2'-azobis(2-amidinopropane) dihydrochloride as an azo-based compound, 0.037 g (0.137 mmol) of potassium persulfate as a peroxide, and 0.01012 g (0.058 mmol) of ethylene glycol diglycidyl ether as an internal-crosslinking agent were added thereto and dissolved to prepare an aqueous monomer solution.

The aqueous monomer solution prepared as described above was added to the separable flask, and the atmosphere in the system was thoroughly replaced with nitrogen. The flask was then immersed in a 70° C. water bath to raise the temperature to perform polymerization for 60 minutes to prepare a first-stage polymerized slurry.

Meanwhile, 128.8 g (1.43 mol) of an aqueous 80 mass % acrylic acid solution was put in another 500-mL Erlenmeyer flask, and 159.0 g of an aqueous 27 mass % sodium hydroxide solution was dropwise added thereto while cooling from the outside for neutralization at 75 mol %. Subsequently, 0.129 g (0.475 mmol) of 2,2'-azobis(2-amidinopropane) dihydrochloride as an azo-based compound, 0.052 g (0.191 mmol) of potassium persulfate as a peroxide, and 0.0116 g (0.067 mmol) of ethylene glycol diglycidyl ether as an internal-crosslinking agent were added thereto and dissolved to prepare a second-stage aqueous monomer solution.

The inside of the above-described separable flask system was cooled to 25° C., and the whole quantity of the second-stage aqueous monomer solution was then added to the first-stage polymerized slurry. The atmosphere in the system was thoroughly replaced with nitrogen, and the flask was then immersed in a 70° C. water bath again to raise the temperature to perform second-stage polymerization for 30 minutes.

To the hydrous gel after the second-stage polymerization added was 2.76 g of an aqueous 40 mass % hexasodium triethylenetetraminehexaacetate solution with stirring. Subsequently, the temperature of the reaction solution was raised with a 125° C. oil bath, and 240 g of water was removed to the outside of the system by azeotropic distillation of n-heptane and water while refluxing n-heptane. Subsequently, 4.42 g (0.51 mmol) of an aqueous 2 mass % ethylene glycol diglycidyl ether solution was added thereto as a post-crosslinking agent, and the mixture was maintained at 80° C. for 2 hours. Subsequently, drying step was performed by evaporating the n-heptane to obtain a dried resin. This dried resin was allowed to pass through a sieve with openings of 1000 μm to obtain 232.3 g of a water-absorbent resin in a form of agglomerated spherical particles. The thus-prepared water-absorbent resin was evaluated in accordance with each type of the above-described test methods. The resulting water-absorbent resin had a median particle diameter of 395 μm.

Example 4

Example 4 was performed as in Example 3 except that the amount of the aqueous 40 mass % hexasodium triethylenetetraminehexaacetate solution to be added after the second-stage polymerization was changed to 0.83 g. The thus-prepared 231.8 g of water-absorbent resin was evaluated in accordance with each type of the above-described test methods. The resulting water-absorbent resin had a median particle diameter of 375 μm.

Example 5

A 2 L cylindrical round-bottom separable flask having an inner diameter of 110 mm and equipped with a reflux condenser, a dropping funnel, a nitrogen gas-introducing tube, and stirrer having stirring blades compound of two sets of 4 inclined paddle blades with a blade diameter of 50 mm was prepared. Into this flask added were 300 g of n-heptane as a hydrocarbon dispersion medium, 0.74 g of HLB3 sucrose stearic acid ester (made by Mitsubishi-Kagaku Foods Corporation, Ryoto sugar ester S-370) as a surfactant, and 0.74 g of maleic anhydride modified ethylene-propylene copolymer (made by Mitsui Chemicals, Inc., High Wax 1105A) as a polymeric dispersion agent. The mixture was heated to 80° C. with stirring to dissolve the surfactant and was then cooled to 55° C.

Meanwhile, 92 g (1.02 mol) of an aqueous 80 mass % acrylic acid solution was put in a 500-mL Erlenmeyer flask, and 146.0 g of an aqueous 21 mass % sodium hydroxide solution was dropwise added thereto while cooling from the outside for neutralization at 75 mol %. Subsequently, 0.110 g (0.406 mmol) of 2,2'-azobis(2-amidinopropane) dihydrochloride as an azo-based compound, 0.037 g (0.137 mmol) of potassium persulfate as a peroxide, and 0.014 g (0.080 mmol) of ethylene glycol diglycidyl ether as an internal-crosslinking agent were added thereto and dissolved to prepare an aqueous monomer solution.

The aqueous monomer solution prepared as described above was added to the separable flask, and the atmosphere in the system was thoroughly replaced with nitrogen. The flask was then immersed in a 70° C. water bath to raise the temperature to perform polymerization for 60 minutes.

To the hydrous gel after the polymerization added was 1.21 g of an aqueous 38 mass % tetrasodium ethylenediaminetetraacetate solution with stirring. Subsequently, the temperature of the polymerization reaction solution was raised with a 125° C. oil bath, and 116 g of water was removed to the outside of the system by azeotropic distillation of water and n-heptane while refluxing n-heptane. Subsequently, 3.68 g (0.423 mmol) of an aqueous 2 mass % ethylene glycol diglycidyl ether solution was added thereto as a post-crosslinking agent, and the mixture was maintained at 80° C. for 2 hours. Subsequently, drying step was performed by evaporating the n-heptane to obtain a dried resin. This dried resin was allowed to pass through a sieve with openings of 1000 μm to obtain 95.1 g of a spherical water-absorbent resin. The thus-prepared water-absorbent resin was evaluated in accordance with each type of the above-described test methods. The resulting water-absorbent resin had a median particle diameter of 120 μm.

Example 6

A 2-L cylindrical round-bottom separable flask having an inner diameter of 110 mm and equipped with a reflux condenser, a dropping funnel, a nitrogen gas-introducing tube, and stirrer having stirring blades compound of two sets of 4 inclined paddle blades with a blade diameter of 50 mm was prepared. Into this flask added were 300 g of n-heptane, 0.74 g of HLB3 sucrose stearic acid ester (made by Mitsubishi-Kagaku Foods Corporation, Ryoto sugar ester S-370) as a surfactant, and 0.74 g of maleic anhydride modified ethylene-propylene copolymer (made by Mitsui Chemicals, Inc., High Wax 1105A) as a polymeric dispersion agent. The mixture was heated to 80° C. with stirring to dissolve the surfactant and was then cooled to 50° C.

Meanwhile, 92 g (1.02 mol) of an aqueous 80 mass % acrylic acid solution was put in a 500-mL Erlenmeyer flask, and 146.0 g of an aqueous 21 mass % sodium hydroxide solution was dropwise added thereto while cooling from the outside for neutralization at 75 mol %. Subsequently, 0.092 g of hydroxyethyl cellulose (made by Sumitomo Seika Chemicals Co., Ltd., HEC AW-15F) as a thickener, 0.101 g (0.372 mmol) of 2,2'-azobis(2-amidinopropane) dihydrochloride as an azo-based compound, 0.028 g (0.104 mmol) of potassium persulfate as a peroxide, and 0.01012 g (0.058 mmol) of ethylene glycol diglycidyl ether as an internal-crosslinking agent were added thereto and dissolved to prepare an aqueous monomer solution.

The aqueous monomer solution prepared as described above was added to the separable flask, and the atmosphere in the system was thoroughly replaced with nitrogen. The flask was then immersed in a 70° C. water bath to raise the temperature to perform polymerization for 60 minutes to obtain a first-stage polymerized slurry.

Meanwhile, 128.8 g (1.43 mol) of an aqueous 80 mass % acrylic acid solution was put in another 500-mL Erlenmeyer flask, and 159.0 g of an aqueous 27 mass % sodium hydroxide solution was dropwise added thereto while cooling from the outside for neutralization at 75 mol %. Subsequently, 0.142 g (0.524 mmol) of 2,2'-azobis(2-amidinopropane) dihydrochloride as an azo-based compound, 0.039 g (0.144 mmol) of potassium persulfate as a peroxide, and 0.0116 g (0.067 mmol) of ethylene glycol diglycidyl ether as an internal-crosslinking agent were added thereto and dissolved to prepare a second-stage aqueous monomer solution.

The inside of the above-described separable flask system was cooled to 25° C., and the whole quantity of the second-stage aqueous monomer solution was then added to the first-stage polymerized slurry. The atmosphere in the system was thoroughly replaced with nitrogen, and the flask was then immersed in a 70° C. water bath again to raise the temperature to perform second-stage polymerization for 30 minutes.

To the hydrous gel after the second-stage polymerization added was 0.83 g of an aqueous 40 mass % pentasodium diethylenetriaminepentaacetate solution with stirring. Subsequently, the temperature of the reaction solution was raised with a 125° C. oil bath, and 242 g of water was removed to the outside of the system by azeotropic distillation of n-heptane and water while refluxing n-heptane. Subsequently, 4.42 g (0.51 mmol) of an aqueous 2 mass % ethylene glycol diglycidyl ether solution was added thereto as a post-crosslinking agent, and the mixture was maintained at 80° C. for 2 hours. Subsequently, drying step was performed by evaporating the n-heptane to obtain a dried resin. This dried resin was allowed to pass through a sieve with openings of 1000 μm to obtain 231.5 g of a water-absorbent resin in a form of agglomerated spherical particles. The thus-prepared water-absorbent resin was evaluated in accordance with each type of the above-described test methods. The resulting water-absorbent resin had a median particle diameter of 360 μm.

Example 7

Example 7 was performed as in Example 6 except that the aminocarboxylic acid compound to be added after the second-stage polymerization was changed to 3.68 g of an aqueous 40 mass % trisodium hydroxyethylethylenediaminetriacetate and that the amount of water to be removed by azeotropic distillation was changed to 237 g. The thus-prepared 233.1 g of water-absorbent resin was evaluated in accordance with each type of the above-described test methods. The resulting water-absorbent resin had a median particle diameter of 410 μm.

Comparative Example 1

In Comparative Example 1, a 2-L cylindrical round-bottom separable flask having an inner diameter of 110 mm and equipped with a reflux condenser, a dropping funnel, a nitrogen gas-introducing tube, and stirrer having stirring blades compound of two sets of 4 inclined paddle blades with a blade diameter of 50 mm was prepared. Into this flask added were 300 g of n-heptane, 0.74 g of HLB3 sucrose stearic acid ester (made by Mitsubishi-Kagaku Foods Corporation, Ryoto sugar ester S-370) as a surfactant, and 0.74 g of maleic anhydride modified ethylene-propylene copolymer (made by Mitsui Chemicals, Inc., High Wax 1105A) as a polymeric dispersion agent. The mixture was heated to 80° C. with stirring to dissolve the surfactant and was then cooled to 50° C.

Meanwhile, 92 g (1.02 mol) of an aqueous 80 mass % acrylic acid solution was put in a 500-mL Erlenmeyer flask, and 146.0 g of an aqueous 21 mass % sodium hydroxide solution was dropwise added thereto while cooling from the outside for neutralization at 75 mol %. Subsequently, 0.092 g of hydroxylethyl cellulose (made by Sumitomo Seika Chemicals Co., Ltd., HEC AW-15F) as a thickener, 0.110 g (0.407 mmol) of 2,2'-azobis(2-amidinopropane) dihydrochloride as an azo-based compound, and 0.01012 g (0.058 mmol) of ethylene glycol diglycidyl ether as an internal-crosslinking agent were added thereto and dissolved to prepare an aqueous monomer solution.

The aqueous monomer solution prepared as described above was added to the separable flask, and the atmosphere in the system was thoroughly replaced with nitrogen. The flask was then immersed in a 70° C. water bath to raise the temperature to perform polymerization for 60 minutes to prepare a first-stage polymerized slurry.

Meanwhile, 128.8 g (1.43 mol) of an aqueous 80 mass % acrylic acid solution was put in another 500-mL Erlenmeyer flask, and 159.0 g of an aqueous 27 mass % sodium hydroxide solution was dropwise added thereto while cooling from the outside for neutralization at 75 mol %. Subsequently, 0.155 g (0.572 mmol) of 2,2'-azobis(2-amidinopropane) dihydrochloride as an azo-based compound and 0.0116 g (0.067 mmol) of ethylene glycol diglycidyl ether as an internal-crosslinking agent were added thereto and dissolved to prepare a second-stage aqueous monomer solution.

The inside of the above-described separable flask system was cooled to 25° C., and the whole quantity of the second-stage aqueous monomer solution was then added to the first-stage polymerized slurry. The atmosphere in the system was thoroughly replaced with nitrogen, and the flask was then immersed in a 70° C. water bath again to raise the temperature to perform second-stage polymerization for 30 minutes.

After the second-stage polymerization, the temperature of the reaction solution was raised with a 125° C. oil bath, and 240 g of water was removed to the outside of the system by azeotropic distillation of n-heptane and water while refluxing n-heptane. Subsequently, 4.42 g (0.51 mmol) of an aqueous 2 mass % ethylene glycol diglycidyl ether solution was added thereto as a post-crosslinking agent, and the mixture was maintained at 80° C. for 2 hours. Subsequently, drying step was performed by evaporating the n-heptane to obtain a dried resin. This dried resin was allowed to pass through a sieve with openings of 1000 μm to obtain 231.1 g of a water-absorbent resin in a form of agglomerated spherical particles. The thus-prepared water-absorbent resin was evaluated in accordance with each type of the above-described test methods. The resulting water-absorbent resin had a median particle diameter of 355 μm.

Comparative Example 2

Comparative Example 2 was performed as in Comparative Example 1 except that 2.76 g of an aqueous 40 mass % hexasodium triethylenetetraminehexaacetate solution was added to the hydrous gel after the second-stage polymerization with stirring. The thus-prepared 232.2 g of water-absorbent resin was evaluated in accordance with each type of the above-described test methods. The resulting water-absorbent resin had a median particle diameter of 380 μm.

Comparative Example 3

Comparative Example 3 was performed as in Comparative Example 2 except that the aminocarboxylic acid compound to be added after the second-stage polymerization was changed to 0.83 g of an aqueous 40 mass % pentasodium diethylenetriaminepentaacetate solution and that the amount of water to be removed by azeotropic distillation was changed to 236 g. The thus-prepared 231.6 g of water-absorbent resin was evaluated in accordance with each type of the above-described test methods. The resulting water-absorbent resin had a median particle diameter of 365 μm.

4-3. Results of Evaluation

Table 1 below shows the results of evaluation of the water-absorbent resins prepared in Examples 1 to 7 and Comparative Examples 1 to 3. Table 1 summarizes desirable physical properties: water-absorption capacity under both no load and load condition, residual monomer content, initial value of yellow index, and yellow index change ratio (discoloration test under 70° C. and 90% RH).

TABLE 1

|  | a water-absorption capacity of physiological saline (g/g) | a water-absorption capacity of physiological saline under a load of 4.14 kPa (ml/g) | Residual monomer content (ppm) | Initial value of yellow index | Yellow index change ratio (Discoloration test under 70° C. and 90% RH) | | | |
| --- | --- | --- | --- | --- | --- | --- | --- | --- |
|  |  |  |  |  | After 7 days | After 10 days | After 14 days | After 21 days |
| Example 1 | 82 | 20 | 80 | 2.9 | 6.7 | 9.4 | 15.1 | 23.5 |
| Example 2 | 64 | 21 | 75 | 3.3 | 5.2 | 7.7 | 12.4 | 17.9 |
| Example 3 | 64 | 22 | 60 | 4.7 | 1.4 | 1.9 | 2.9 | 5.2 |
| Example 4 | 63 | 23 | 85 | 4.5 | 1.4 | 1.9 | 3.0 | 5.4 |
| Example 5 | 60 | 23 | 80 | 3.7 | 2.0 | 3.0 | 4.2 | 7.1 |
| Example 6 | 68 | 16 | 70 | 4.4 | 1.3 | 2.0 | 3.0 | 5.5 |
| Example 7 | 61 | 25 | 75 | 4.2 | 1.6 | 2.2 | 3.3 | 6.7 |
| Comparative Example 1 | 58 | 18 | 380 | 0.8 | 36.3 | 54.5 | 92.5 | 107.4 |
| Comparative Example 2 | 61 | 20 | 320 | 1.1 | 4.8 | 11.7 | 17.4 | 36.5 |
| Comparative Example 3 | 57 | 23 | 360 | 0.9 | 5.8 | 14.8 | 22.7 | 47.0 |

EXPLANATION OF REFERENCE NUMERALS

X measurement apparatus
1 buret part
2 conduit
3 measurement stage
4 measurement part
5 water-absorbent resin

The invention claimed is:

1. A water-absorbent resin prepared by polymerizing a water-soluble ethylenically unsaturated monomer in the presence of an internal crosslinking agent and performing post-crosslinking with a post-crosslinking agent, wherein
  a monomer of 70 to 100 mol % in the water-soluble ethylenically unsaturated monomer is acrylic acid or salt thereof;
  the post-crosslinking agent is at least one selected from the group consisting of (poly)ethylene glycol diglycidyl ethers, (poly)glycerin diglycidyl ethers, (poly) glycerin triglycidyl ethers, trimethylolpropane triglycidyl ethers, (poly)propylene glycol polyglycidyl ethers, and (poly)glycerol polyglycidyl ethers;
  both an azo-based compound and a peroxide are present in the same stage of the polymerization; and
  the water-absorbent resin satisfies all of the following properties:
  (A) a water-absorption capacity of physiological saline of 55 g/g or more, a water-absorption capacity of physiological saline under a load of 4.14 kPa of 15 mL/g or more, and a residual monomer content of 300 ppm or less; and (B) a yellow index of 5.0 or less and a yellow index change ratio (ΔYI) after leaving for 10 days under 70° C. and 90% RH of 10 or less.

2. The water-absorbent resin according to claim 1, having a median particle diameter of 100 to 600 μm.

3. An absorbent article comprising an absorbent material including the water-absorbent resin according to claim 1.

4. The water-absorbent resin according to claim 1, performing the polymerization in a single stage in the presence of an internal-crosslinking agent and in the presence of both an azo-based compound and a peroxide.

* * * * *